United States Patent
Mirhassani et al.

(10) Patent No.: US 12,422,395 B2
(45) Date of Patent: Sep. 23, 2025

(54) CAPACITANCE VARIATION MEASUREMENT MIXED SIGNAL IC BASED ON HIGH-FREQUENCY RESPONSE

(71) Applicant: University of Windsor, Windsor (CA)

(72) Inventors: Mitra Mirhassani, LaSalle (CA); Hamidreza Esmaeili Taheri, Markham (CA)

(73) Assignee: UNIVERSITY OF WINDSOR, Windsor (CA)

(*) Notice: Subject to any disclaimer, the term of this patent is extended or adjusted under 35 U.S.C. 154(b) by 222 days.

(21) Appl. No.: 18/315,203

(22) Filed: May 10, 2023

(65) Prior Publication Data

US 2023/0366847 A1  Nov. 16, 2023

Related U.S. Application Data

(60) Provisional application No. 63/340,165, filed on May 10, 2022.

(51) Int. Cl.
    *G01N 27/22*  (2006.01)
    *G01D 5/24*   (2006.01)
    *G01R 27/26*  (2006.01)

(52) U.S. Cl.
    CPC ......... *G01N 27/228* (2013.01); *G01D 5/24* (2013.01); *G01R 27/2605* (2013.01); *G01N 27/22* (2013.01); *G01R 27/26* (2013.01)

(58) Field of Classification Search
    CPC ........ G01R 27/00; G01R 27/02; G01R 27/26; G01N 27/00; G01N 27/02; G01N 27/22; G01N 27/228; G01N 27/48; G01N 27/483; G01N 27/4833; G01N 27/487; G01N 27/48707; G01D 5/00; G01D 5/12; G01D 5/14; G01D 5/24
    USPC ....... 324/600, 649, 658, 686, 500, 512, 519, 324/537, 548
    See application file for complete search history.

(56) References Cited

U.S. PATENT DOCUMENTS

11,437,993 B2 * 9/2022 Kubo .................. G01D 5/241

FOREIGN PATENT DOCUMENTS

| DE | 4224545 A1 * | 1/1993 | ......... G01R 27/2605 |
| WO | WO-2008064500 A2 * | 6/2008 | ............ G01D 3/036 |
| WO | WO-2016208678 A1 * | 12/2016 | ............... G01D 5/12 |

OTHER PUBLICATIONS

Lei, Ka-Meng, et al. "CMOS biosensors for in vitro diagnosis—transducing mechanisms and applications." Lab on a Chip 16.19 (2016): 3664-3681.

(Continued)

*Primary Examiner* — Hoai-An D. Nguyen (57) ABSTRACT

In a preferred embodiment, there is provided a method for measuring a capacitance change or difference of a sensing capacitor, the method comprising: sweeping a frequency range of first and second alternating current (AC) voltage sources respectively connected to first and second amplifiers, said first amplifier having or connected to a first reference capacitor or electrode and said second amplifier having or connected to a second reference capacitor or electrode and the sensing capacitor; detecting first and second high cutoff frequencies respectively of the first and second amplifiers; and determining a difference between the first and second high cutoff frequencies, wherein the difference reflects the capacitance change or difference.

24 Claims, 11 Drawing Sheets

(56) References Cited

OTHER PUBLICATIONS

S. B. Prakash and P. Abshire, "Tracking cancer cell proliferation on a CMOS capacitance sensor chip," Biosensors Bioelectron., vol. 23, No. 10, pp. 1449-1457, 2008.

K. Lee et al., "CMOS capacitive biosensor with enhanced sensitivity for label-free DNA detection," in Proc. ISSCC, San Francisco, Cal, USA, 2012, pp. 1-4.

A. Balasubramanian et al., "Si-Based sensor for virus detection," IEEE Sens. J., vol. 5, No. 3, pp. 340-344, Jun. 2005.

C. Xiao, and J. H. T. Luong, "On-line monitoring of cell growth and cytotoxicity using electric cell-substrate impedance sensing (ECIS)," Biotechnol. Progress, vol. 19, No. 3, pp. 1000-1005, 2003.

H. Mazhab-Jafari, L. Soleymani, and R. Genov, "16-Channel CMOS impedance spectroscopy DNA analyzer with dual-slope multiplying ADCs," IEEE Trans. Biomed. Circuits Syst., vol. 6, No. 5, pp. 468-478, Apr. 2012.

N. Couniot et al., "A capacitance to frequency converter with on-chip passivated microelectrodes for bacteria detection n saline buffers up to 575 MHz," IEEE Trans. Circuits Syst., II, Exp. Briefs, vol. 62, No. 2, pp. 159-163, Feb. 2015.

I. Evans, and T. York, "Microelectronic capacitance transducer for particle detection," IEEE Sens. J., vol. 4, No. 3, pp. 364-372, Jun. 2004.

D. Sylvester, J. C. Chen, and C. Hu, "Investigation of interconnect capacitance characterization using charge-based capacitance measurement (CBCM) technique and three-dimensional simulation," IEEE J. Solid-State Circuits, vol. 33, No. 3, pp. 449-453, Mar. 1998.

S. B. Parkash, and P. Abshire, "On-chip capacitance sensing for cell monitoring applications," IEEE Sens. J., IEEE Sens. J., vol. 7, No. 3, pp. 440-447, Mar. 2007.

B. P. Senevirathna et al., "Real-time measurements of cell proliferation using a lab-on-CMOS capacitance sensor array," IEEE Trans. Biomed. Circuits Syst., vol. 12, No. 3, pp. 510-520, Jun. 2018.

A. Bahnson et al., "Automated measurement of cell mobility and proliferation," BMC Cell Biol., vol. 6, No. 1, Apr. 2005.

G. Nabovti et al., "Towards high throughput cell growth screening: A new CMOS 8*8 biosensor array for life science applications," IEEE Trans. Biomed. Circuits Syst., vol. 11, No. 2, pp. 380-391, Apr. 2017.

B. Senevirathna, S. Lu, and P. Abshire, "Characterization of a high dynamic range lab-on-CMOS capacitance sensor array," in Proc. ISCAS, Baltimore, MD, USA, 2017, pp. 1-4.

S. B. Parkash, and P. Abshire, "A fully differential rail-to-rail CMOS capacitance sensor with floating-gate trimming for mismatch compensation," IEEE T. Circuits—I, vol. 56, No. 5, pp. 957-986, May 2009.

E. Ghafar-Zadeh et al., "Bacteria Growth Monitoring Through a Differential CMOS Capacitive Sensor," IEEE Trans. Biomed. Circuits Syst., vol. 4, No. 4, pp. 232-238, Aug. 2010.

De Marcellis, A.; Reig, C.; Cubells-Beltrán, M.-D. A Capacitance-to-Time Converter-Based Electronic Interface for Differential Capacitive Sensors. Electronics 2019, 8, 80.

A. Arshad, R. Tasnim, A. H. M. Z. Alam and S. Khan, "Capacitance-to-voltage converter design to measure small change in capacitance produced by human body movement," 2015 IEEE International WIE Conference on Electrical and Computer Engineering (WIECON-ECE), Dhaka, Bangladesh, 2015, pp. 114-117.

Yusmeeraz Yusof et al, "On-chip Microelectrode Capacitance Measurement for Biosensing Applications", 2010 Jpn. J. Appl. Phys. 49 01AG05.

Lu et al., "5 x 5 CMOS capacitive sensor array for detection of the neurotransmitter dopamine", Biosensors and Bioelectronics, vol. 26, Issue 3, Nov. 15, 2010, pp. 1093-1097.

A.S. Sedra, K.C. Smith, T.C. Carusone, and V.Gaudet, Microelectronic circuits. Oxford University Press, 2016.

A.-Y. Chang and M. S.-C. Lu, "A cmos magnetic microbead-based capacitive biosensor array with on-chip electromagnetic manipulation," Biosensors and Bioelectronics, vol. 45, pp. 6-12, 2013.

K.-H. Lee, S. Choi, J. O. Lee, J.-B. Yoon, and G.-H. Cho, "Cmos capacitive biosensor with enhanced sensitivity for label-free dna detection," in 2012 IEEE International Solid-State Circuits Conference. IEEE, 2012, pp. 120-122.

\* cited by examiner

CAPACITANCE VARIATION MEASUREMENT MIXED SIGNAL IC BASED ON HIGH-FREQUENCY RESPONSE

RELATED APPLICATIONS

This application claims the benefit under 35 USC 119(e) to U.S. Provisional Application Ser. No. 63/340,165 filed 10 May 2022, the entire contents of which are incorporated herein by reference.

SCOPE OF THE INVENTION

The present invention relates to a method for measuring a capacitance change or difference of a sensing capacitor, and which includes detecting a high cutoff frequency of a voltage amplifier connected to the sensing capacitor and determining a difference from a reference high cutoff frequency as a measure of the capacitance change or difference.

BACKGROUND OF THE INVENTION

CMOS biosensors have contributed to sensing mechanisms in life science applications. Features of a CMOS sensing microsystem such as low cost, small size, low power consumption and accurate measurement due to noise immunity have shown results in life science applications including, cell growth monitoring, bacteria screening, DNA detection and virus detection. These are some of the interdisciplinary areas that biology, chemistry and microelectronics accompany to address a challenging issue, and microelectronic circuits may be employed for signal reading out and processing. For mentioned applications, several microelectronics solutions have been proposed as the readout system. Among different electrical characteristics that may change during target detection in a sensing system, impedance and capacitance variations, owing to simple measurement techniques, have attracted many circuit designers. Impedance measurement was proposed, where electric cell-substrate impedance is monitored for cell growth detection.

The other electrical variable that has been investigated in sensing systems is capacitance. The fact that when a living organism grows on, or in general a particle adheres to two metal surfaces, the capacitance between these two metals, called sensing electrode capacitance, may change is evident. The remaining challenge is to measure this capacitance variation and translate it to an understandable electrical signal for the rest of the system. This task is not easy because the capacitance variations are in femto-Farad range which is not easy to readout in CMOS circuits due to the parasitic capacitance of MOS transistors. Several efforts have been made to read out small capacitance variations using CMOS integrated circuits. Generally, most of previous works in this field can be categorized into two different groups; 1) Capacitance to Voltage Converters (CVC), and 2) Capacitance to Frequency Converters (CFC).

The main idea in CVC based biosensors is to use a fixed current to charge the variable sensing capacitor. The charging current, which is controlled with two non-overlapping signals, is mirrored to charge an integrating capacitor. The stored charge on the integrating capacitor depends on the charging current, controlling signal period and the value of the sensing capacitance. As the stored charge is changed due to capacitance variation, the voltage on the integrator will change. This voltage variation can be used as a capacitance variation indicator. The CVC approach, which was first reported in as charge based capacitance measurement (CBCM) technique, has been applied to different structures to measure capacitance variations. For instance, this technique is applied to a pair of sensing and reference electrodes, and the voltage difference between sensing and reference integrating capacitors is used as a target detection indicator.

On the other hand, the CFC technique converts the capacitance variations to frequency. Basically, in this method, the sensing electrode is connected between the input and output of an inverter in an inverter chain. As the electrode capacitance changes due to cell growth, the oscillation frequency of the inverter chain will deviate from the free-running value. This frequency variation can be used as target detection indicator.

SUMMARY OF THE INVENTION

A possible non-limiting object of the present invention is to provide a method for measuring a capacitance change or difference in a range as low as a femto-Farad range, and which may be communicated in a discernible electrical signal.

Another possible non-limiting object of the present invention is to provide a method for measuring a capacitance change or difference as may be produced by a sensing capacitor, and which may permit reduction of a noise or error as may be caused by parasitic capacitance in a circuit or by another circuit component.

Another possible non-limiting object of the present invention is to provide a system for measuring a capacitance change or difference, and which may permit improved sensitivity and reduced power consumption.

In a simplified aspect, the present invention provides a method for measuring a capacitance change or difference, the method comprising sweeping a frequency range of a voltage source connected to an amplifier having or connected to a sensing capacitor, detecting a high cutoff frequency of the amplifier, and determining a difference between the high cutoff frequency and a reference high cutoff frequency, wherein the difference reflects the capacitance change or difference.

In another simplified aspect, the present invention provides a method for measuring a capacitance change or difference of a sensing capacitor, the method comprising detecting a high cutoff frequency of an amplifier connected to a voltage source, a reference capacitor and the sensing capacitor, and determining a difference between the high cutoff frequency and a reference high cutoff frequency, wherein the difference reflects the capacitance change or difference, and preferably wherein the reference high cutoff frequency is detected from a further amplifier connected to a further voltage source and a further reference capacitor, the further amplifier, the further voltage source and the further reference capacitor preferably being identical or substantially identical respectively to the amplifier, the voltage source and the reference capacitor.

In another aspect, the present invention provides a method for measuring a capacitance change or difference of a sensing capacitor, the method comprising: sweeping a frequency range of first and second alternating current (AC) voltage sources respectively connected to first and second amplifiers, said first amplifier having or connected to a first reference capacitor or electrode and said second amplifier having or connected to a second reference capacitor or electrode and the sensing capacitor; detecting first and second high cutoff frequencies respectively of the first and second amplifiers; and determining a difference between the first and second high cutoff frequencies, wherein the difference reflects the capacitance change or difference.

In one embodiment, the first and second voltage sources are identical or substantially identical to each other, and the first and second reference capacitors or electrodes are identical or substantially identical to each other. In on embodiment, the first and second amplifiers are identical or substantially identical to each other. In one embodiment, the first and second amplifiers have identical or substantial identical structure.

In one embodiment, the first and second amplifiers comprise first and second common source voltage amplifiers each comprising a cascode current source. In one embodiment, each said common source voltage amplifiers has a gain between about 10 dB and about 500 dB, preferably between about 20 dB and about 300 dB, or more preferably between about 30 dB and about 100 dB.

In one embodiment, the first and second reference capacitors are parallel or in a Miller capacitance location respectively in relation to the first and second amplifiers.

In one embodiment, the sensing capacitor is parallel to the second reference capacitor.

In one embodiment, said detecting the first and second high cutoff frequencies comprises comparing first and second output voltages respectively from the first and second amplifiers to respective first and second reference voltage values, and stopping said sweeping the frequency range when said comparing the first and second output voltages indicates the first and second high cutoff frequencies are reached, wherein the first and second reference voltage values comprise first and second maximum output voltages respectively of the first and second amplifiers. In one embodiment, said detecting the first and second high cutoff frequencies comprises comparing first and second output voltages respectively from the first and second amplifiers to respective first and second reference voltage values, and stopping said sweeping the frequency range when said comparing the first and second output voltages indicates the first and second high cutoff frequencies are reached, wherein the first and second reference voltage values are based on first and second maximum or peak output voltages respectively of the first and second amplifiers.

It is to be appreciated that the high cutoff frequency may be defined by a half-power point, or namely, a frequency at which the output or output voltage is −3 dB of the nominal passband value. The high cutoff frequency may occur when the output voltage has dropped to $1/\sqrt{2}$ (~0.707) of the maximum output voltage and the power has dropped by half. It has been envisioned, however, that the invention may be practiced with the first and second high cutoff frequencies, as well those of other arbitrary frequencies within 20% of the high cutoff frequencies and those of low cutoff frequencies or other arbitrary frequencies within 20% of the low cutoff frequencies. In other words, the invention may be practiced with a difference in frequencies near a boundary of the amplifier's frequency response or bandwidth.

In one embodiment, the method further comprises producing a third output voltage having a period or pulse width proportional to the difference.

In one embodiment, said determining the difference comprises transforming the first and second high cutoff frequencies to first and second square waveforms, and said producing the third output voltage comprises producing the third output voltage with an output voltage waveform having a pulse width proportional to the difference.

In one embodiment, the method further comprises providing the third output voltage to a low pass filter.

Figure 1:
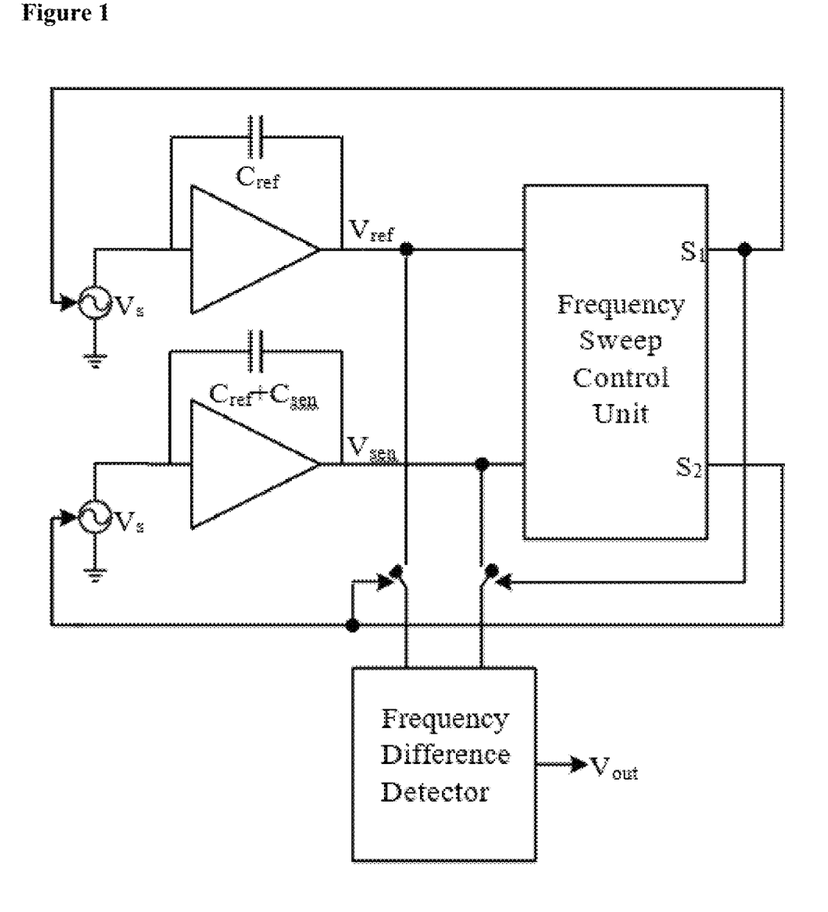
FIG. 1 shows a block diagram of a system in accordance with a preferred embodiment of the present invention.

In one embodiment, the sensing capacitor comprises or comprised in a CMOS biosensor. In one embodiment, the method is for measuring the capacitance change or difference with a CMOS circuit system comprising the first and second voltage sources, the first and second amplifiers, the first and second reference capacitors or electrodes and the sensing capacitor. In one embodiment, the CMOS circuit system is arranged as seen in a block diagram as illustrated in FIG. 1. In one embodiment, the CMOS biosensor is for monitoring cell growth, screening bacteria, detecting DNA or detecting virus.

In yet another aspect, the present invention provides a system for measuring a capacitance change or difference of a sensing capacitor, the system comprising: first and second alternating current (AC) voltage sources; first and second voltage amplifiers respectively connected to the first and second voltage sources, said first amplifier having or connected to a first reference capacitor or electrode and said second amplifier having or connected to a second reference capacitor or electrode and the sensing capacitor; a frequency sweep control unit for sweeping a frequency range of the first and second voltage sources and detecting first and second high cutoff frequencies respectively of the first and second amplifiers; and a frequency difference detector for determining a difference between the first and second high cutoff frequencies, wherein the difference reflects the capacitance change or difference.

In one embodiment, the first and second voltage sources are identical or substantially identical to each other, and the first and second reference capacitors or electrodes are identical or substantially identical to each other. In on embodiment, the first and second voltage amplifiers are identical or substantially identical to each other. In one embodiment, the first and second voltage amplifiers have identical or substantial identical structure.

In one embodiment, the first and second voltage amplifiers comprise first and second common source voltage amplifiers each comprising a cascode current source. In one embodiment, each said common source voltage amplifiers has a gain between about 10 dB and about 500 dB, preferably between about 20 dB and about 300 dB, or more preferably between about 30 dB and about 100 dB.

In one embodiment, the first and second reference capacitors are parallel or in a Miller capacitance location respectively in relation to the first and second voltage amplifiers.

In one embodiment, the sensing capacitor is parallel to the second reference capacitor.

Figure 2:
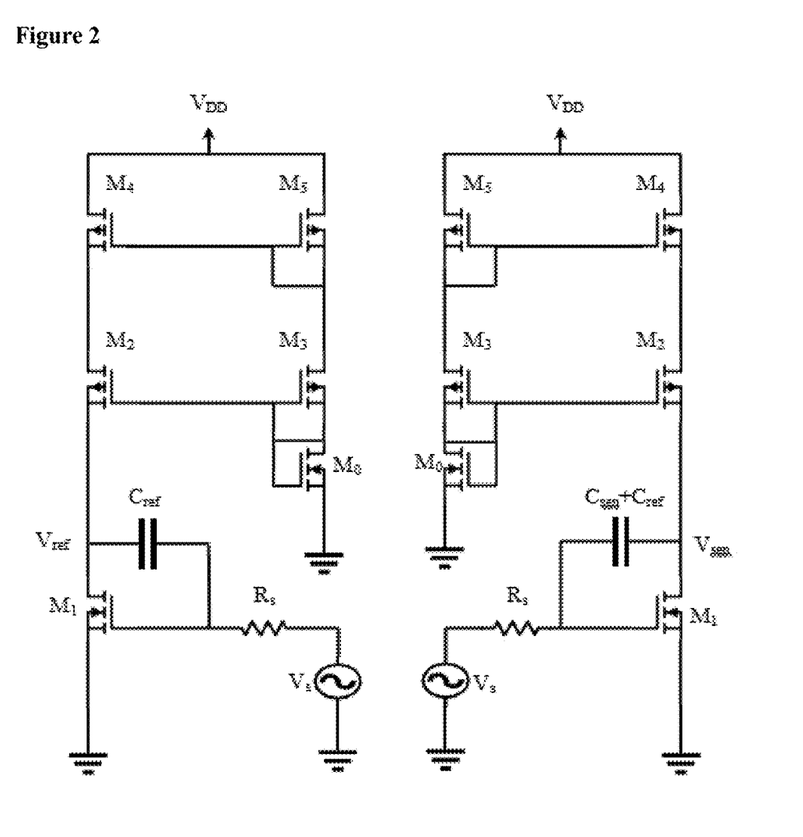
FIG. 2 shows a block diagram of a system in accordance with a preferred embodiment of the present invention, and which includes two identical common source amplifiers with different Miller capacitors.

In one embodiment, the first and second voltage sources and the first and second voltage amplifiers are arranged as seen in a block diagram illustrated in FIG. 1 or 2.

In one embodiment, the frequency sweep control unit comprises first and second voltage comparators and first and second frequency lock detectors respectively connected to the first and second voltage comparators, wherein said first and second voltage comparators are respectively for comparing first and second output voltages respectively from the first and second voltage amplifiers to respective first and second reference voltage values, and said first and second frequency lock detectors are for stopping said sweeping the frequency range and signalling the frequency difference detector to determine the difference upon determining that the first and second high cutoff frequencies are reached, wherein the first and second reference voltage values comprise first and second maximum output voltages respectively of the first and second voltage amplifiers. In one embodiment, the frequency sweep control unit comprises first and second voltage comparators and first and second frequency lock detectors respectively connected to the first and second voltage comparators, wherein said first and second voltage comparators are respectively for comparing first and second output voltages respectively from the first and second voltage amplifiers to respective first and second reference voltage values, and said first and second frequency lock detectors are for stopping said sweeping the frequency range and signalling the frequency difference detector to determine the difference upon determining that the first and second high cutoff frequencies are reached, wherein the first and second reference voltage values are based on first and second maximum output voltages respectively of the first and second voltage amplifiers.

Figure 6:
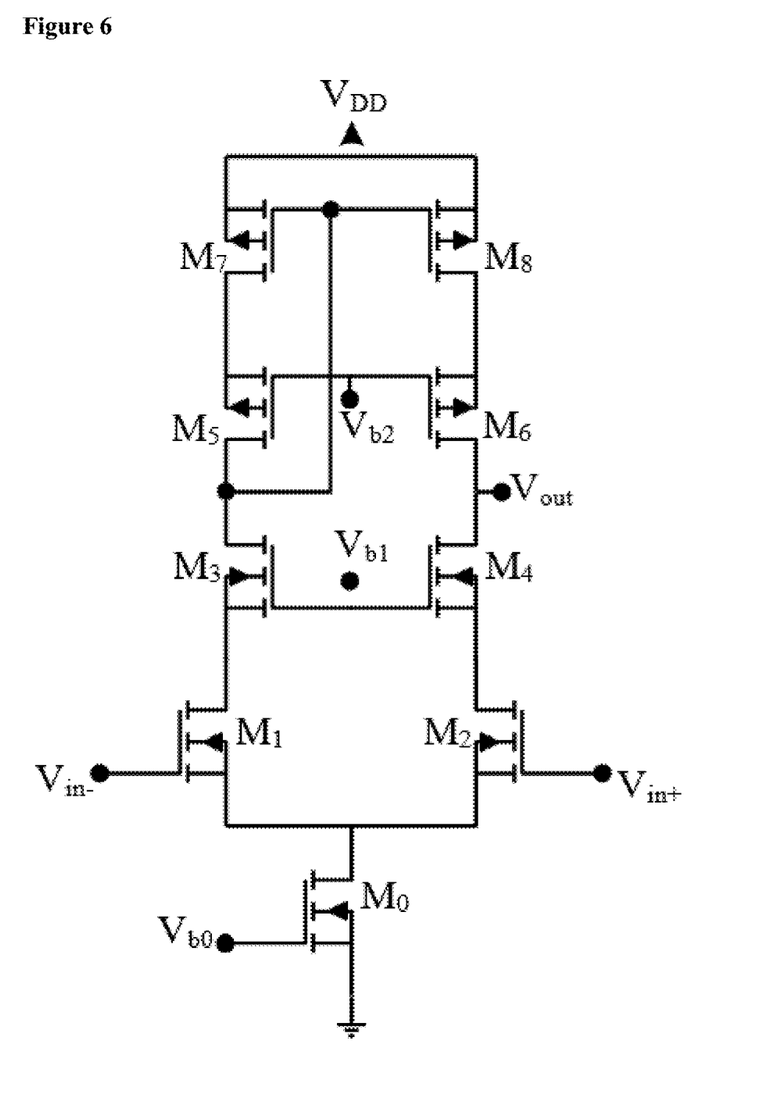
FIG. 6 shows a two-stage voltage comparator in a frequency sweep control unit in accordance with a preferred embodiment of the present invention.

In one embodiment, each said first and second voltage comparators comprise components or a circuit as illustrated in FIG. 6. In one embodiment, the first and second voltage comparators are identical or substantially identical to each other. In one embodiment, each said first and second voltage comparators has a gain between about 20 dB and about 500 dB, preferably between about 30 dB and about 300 dB, or more preferably between about 40 dB and about 100 dB. In one embodiment, each of said first amplifier and first voltage comparator and said second amplifier and second voltage comparator has a combined gain between about 30 dB and about 1000 dB, preferably between about 50 dB and about 600 dB, or more preferably between about 70 dB and about 200 dB.

Figure 5:
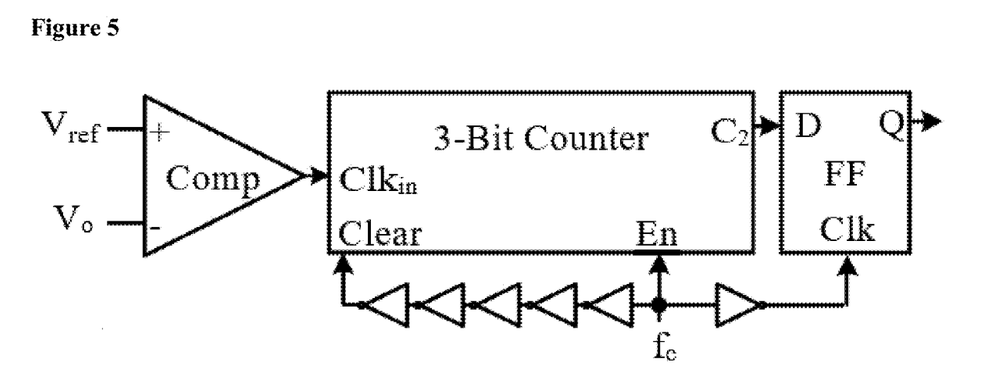
FIG. 5 shows a block diagram of a frequency lock detector in accordance with a preferred embodiment of the present invention.

In one embodiment, the first and second frequency lock detectors comprise respective first and second counters and respective first and second frequency lock detection flags, wherein each said first counter and frequency lock detection flag and second counter and frequency lock detection flag are arranged as illustrated in FIG. 5.

Figure 8:
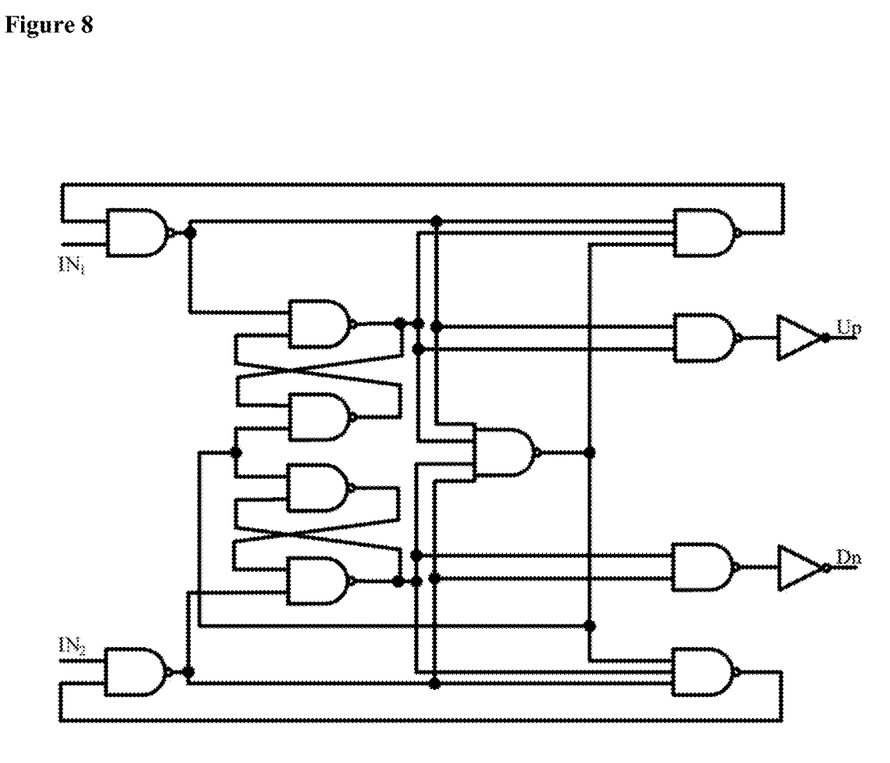
FIG. 8 shows a block diagram of a phase-frequency detector in a frequency difference detector unit in accordance with a preferred embodiment of the present invention.

In one embodiment, the frequency difference detector comprises third and fourth voltage comparators and a phase frequency detector connected to the third and fourth voltage comparators, wherein the third and fourth voltage comparators are for transforming the first and second high cutoff frequencies to first and second square waveforms, and the phase frequency detector is for producing a third output voltage with an output voltage waveform having a pulse width proportional to the difference. In one embodiment, the frequency difference detector comprises third and fourth voltage comparators and a phase frequency detector connected to the third and fourth voltage comparators, wherein the third and fourth voltage comparators are for transforming the first and second high cutoff frequencies to first and second waveforms, and the phase frequency detector is for producing an output waveform having a pulse width proportional to the difference. In one embodiment, the first and second waveforms respectively have first and second waveform frequencies equal to or substantially equal to the first and second high cutoff frequencies. In one embodiment, the first and second waveforms have respective frequencies corresponding to the first and second high cutoff frequencies, and the output waveform has the pulse width proportional to a difference between the respective frequencies of the first and second waveforms. In one embodiment, the phase frequency detector comprises components or a circuit as illustrated in FIG. 8. In one embodiment, the third and fourth voltage comparators are identical or substantially identical to each other.

In one embodiment, the system further comprises a low pass filter arranged to receive the third output voltage from the phase frequency detector.

In one embodiment, the first and second reference capacitors and the sensing capacitor comprise off-chip first and second reference capacitors and the sensing capacitor.

In one embodiment, the sensing capacitor comprises or comprised in a CMOS biosensor. In one embodiment, the system comprises a CMOS circuit. In on embodiment, the system or the components thereof are arranged as seen in a block diagram as illustrated in FIG. 1. In one embodiment, the CMOS biosensor is for monitoring cell growth, screening bacteria, detecting DNA or detecting virus.

In one embodiment, the frequency range comprises for each said first and second voltage sources respective bandwidths of the first and second amplifiers.

BRIEF DESCRIPTION OF THE DRAWINGS

Reference may now be had to the following detailed description taken together with the accompanying drawings in which.

DETAILED DESCRIPTION OF THE PREFERRED EMBODIMENTS

Described herein is a method for measuring a capacitance variation preferably in a life science sensing application. The method is based on the detection of higher cutoff frequency variation of a voltage amplifier due to capacitance variations. Using a fully differential structure, which enables the architecture to cancel-out common mode errors, capacitance variations measurement is performed in two different phases. The first phase sweeps the frequency and the second one detects the capacitance variation value. The method was verified using post-layout simulations in 180 nm CMOS technology and simulation results were produced. With power consumption of 792 μW from 1.8 V supply, the method may permit for low power portable applications.

It has been appreciated that a different technique may be used for capacitance variation detection, where in the architecture, which is based on the high cutoff frequency detection, converts capacitance variation to pulse width variation. The frequency response of an amplifier is basically determined by the high and low frequency poles of the transfer function of the amplifier. When the capacitance connected to a node in an amplifier changes, the cutoff frequency of the amplifier, or in other words, the bandwidth of the amplifier will change. This effect is employed as an indicator for capacitance variations and the required system for detection of the bandwidth variations and conversion of these variations to detectable pulse widths has been designed.

Capacitance to Pulse Width Conversion Technique

It has been appreciated that in a preferred embodiment, a capacitance to pulse width conversion (CPC) technique may be used to detect the variations of high cutoff frequency in an amplifier due to capacitance variations. The higher cutoff frequency of an amplifier may be approximated using equation (1) below:

$$f_H = \frac{1}{2\pi \sum_{i=1}^{n} R_i \times C_i} \quad (1)$$

where n is the number of the high-frequency capacitances in the circuit, $R_i$ is the ac equivalent resistance seen from $C_i$ view, and $C_i$ is the $i_{th}$ high-frequency capacitor. According to equation (1), any change in the value of $C_i$ or $R_i$ result in change in the higher cutoff frequency of the amplifier. In other words, the capacitance variations result in alteration of the frequency of one of the high-frequency poles in the transfer function of the amplifier, which changes the frequency response of the amplifier. Thus, this pole frequency variations may be interpreted as capacitance variations. However, high-frequency pole variations are not significant for small changes in capacitance. Moreover, the value of the variable capacitance is not the only parameter that determines the higher cutoff frequency of the system, because as it is evident in equation (1), all high-frequency capacitors have some contribution.

To use high-frequency pole variations for capacitance sensing, a configuration may be selected that sees the variable capacitance pole as its dominant pole. A dominant pole is a high-frequency pole in the amplifier transfer function which has the most significant role in high cutoff frequency determination. So, to use the high-frequency pole variations as the capacitance variation indicator, the variable capacitance may be placed at a location that produces the dominant high-frequency pole of the amplifier. This location may be the Miller capacitance location of an amplifier.

To use high cutoff frequency variations for capacitance measurement, a system with the block diagram of FIG. 1 may be used. To achieve benefits of differential structures which can cancel-out common mode based errors, two identical amplifier stages are used. One amplifier has a reference capacitor (or electrode) in its Miller position, while the other one sees sensing, unknown capacitor in parallel to the same reference capacitor. Since the two amplifiers have the same input amplitude and same structure, and their unique difference is the Miller capacitance, their only difference is the high cutoff frequency. To extract this high cutoff frequency difference, two amplifiers with two identical input voltage sources were used, as seen in FIG. 1. It was operated to sweep the frequency of the two input voltage sources until the output amplitude of the amplifier stage is equal to the value of the output at high cutoff frequency. This was the point frequency sweep stopped and frequency difference detection was initiated. To detect the frequency-sweep stop point, the two outputs of the voltage amplifiers were applied to a frequency sweep control unit (FSCU) that is employed to identify the high cutoff frequency of the voltage amplifiers. The FSCU produces two output signals which indicate that the applied input frequencies are equal to the higher cutoff frequency of the two amplifiers. When the outputs of the FSCU are high, the sweep frequency phase of the corresponding amplifier will stop and at the same time, the output of the amplifier is applied to a frequency difference detector (FDD). The duty of FDD is to produce an output voltage which its pulse width is proportional to the frequency difference of its two inputs. Since the input frequencies of the FDD are a measure of the sensing and reference capacitance, the FDD output pulse width is unique for each value of the sensing capacitor and is reported as the output of the sensing system.

Building Blocks of the Proposed Measurement Technique

In spite of the two amplifiers shown in FIG. 1, a FSCU and a FDD unit are required. The two amplifiers used in the structure are common source (CS) amplifiers. The FSCU is composed of two identical voltage comparators with small propagation delay, and two identical frequency lock detection (FLD) units, followed by a FLD flag. The FDD is composed of two voltage comparators and a phase-frequency detector (PFD), as described below.

Common Source Amplifiers with Active Load

Figure 3:
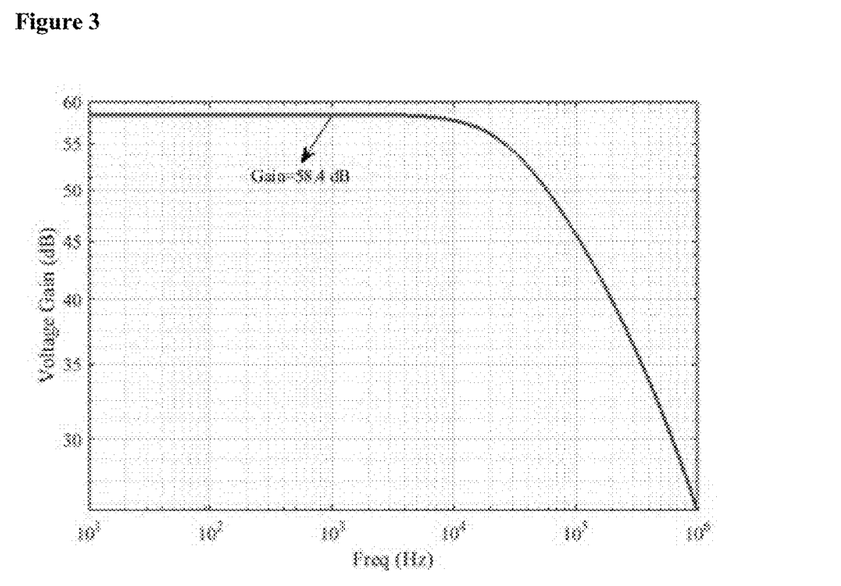
FIG. 3 shows a frequency response of the CS amplifier with $C_{ref}=10$ fF.
Figure 4:
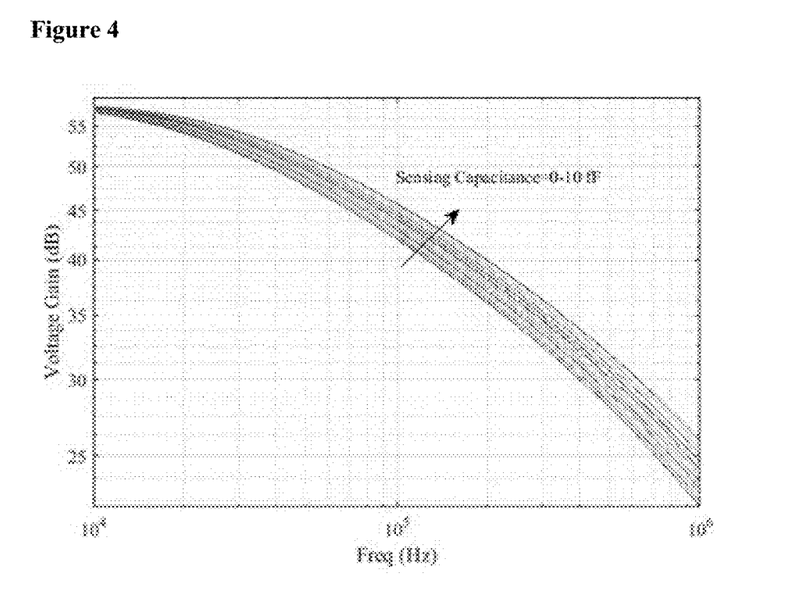
FIG. 4 shows high cutoff frequency variation in the CS amplifier due to $C_{sen}=0-10$ fF.

For the capacitance measurement technique, two simple Common Source (CS) voltage amplifiers were used, as seen in FIG. 2. The load of the CS amplifier is a cascode current source, which delivers the highest possible load to the amplifier and allows the amplifying transistor to be able to reach its intrinsic gain. As noted above, to obtain a fully differential configuration that is more immune to common mode errors and is able to detect the baseline value of the higher cutoff frequency, two identical CS amplifiers were designed, one of which sees the sensing variable capacitance in parallel to a fixed reference capacitance at its Miller location, while the other one just sees the reference Miller capacitance, as seen in FIG. 2. The CS amplifier seen in FIG. 2 preferably has a voltage gain as high as possible. The two CS amplifiers showed the gain of 58.43 dB in the frequency band of interest as seen in FIG. 3. For $C_{ref}$=10 fF, and $C_{sen}$=0-10 fF, FIG. 4 shows the variations in the high cutoff frequency of CS amplifier. The capacitance variation has resulted in $f_H$ variations in the range of 15.16-23.54 KHz. The main performance characteristics of the CS amplifiers are shown in Table I, and Table II shows the transistor dimensions in the CS amplifier.

TABLE I

CS amplifier characteristics

| Parameter | Value |
|---|---|
| DC Gain | 58.43 dB |
| Unity Gain Bandwidth | 24.78 MHz |
| Power Consumption | 358.4 nW |
| Output Voltage Swing | 1.2 $V_{(p-p)}$ |
| Supply Voltage | 1.8 V |

TABLE II

CS amplifier transistor dimensions

| Transistor | Aspect Ratio (w/l) |
|---|---|
| $M_0$ | 0.1 |
| $M_1$ | 1.1 |
| $M_{2,3}$ | 0.1 |
| $M_{4,5}$ | 0.1 |

Frequency Sweep Control Unit (FSCU)

The function of the FSCU block seen in FIG. 1 is to detect the high cutoff frequency of the CS amplifier, and is composed of two identical voltage comparators, and two counters followed by two frequency lock detection flags. The two comparators compare the output voltages of common source amplifiers with a reference value. The outputs of these two comparators are square waveforms. With the input frequency sweep, the amplitude of the output waveform of the CS amplifier decreases, and as a result, the duty cycle of the output square waveform of the comparator will increase. As long as the output waveform of the comparator experiences rising and falling edges, the frequency sweep should continue. When the output square waveform of the comparator, transforms to a logic "1" DC signal (as a result of frequency increase), the frequency sweep should stop. In order to detect this point, the two outputs of the comparators were buffered and applied to two frequency lock detection (FLD) blocks. The FLD block is composed of a counter, and a FLD bit, and is fed with the output of the comparators, and a square waveform clock which its frequency is one tenth of the input frequency, as seen in FIG. 5. During the clock high, the counter counts up. When the clock turns to low, the counting stops, and the most significant bit of the counter is stored in a flip flop, so called FLD flag, and with a delay time the counter resets. If the FLD is high, it means that the output waveform of the comparator has rising edges, which means that the frequency sweep should continue. If the FLD bit is low, it means that the comparator waveform has not rising edges, thus the frequency sweep should stop. So, the final output of the FSCU is a logic control signal, which ends the sweep phase, and initiates frequency difference detection. The outputs of the FSCU, control two switches which apply the output signals of the CS amplifiers to the FDD unit as seen in FIG. 1.

Figure 7:
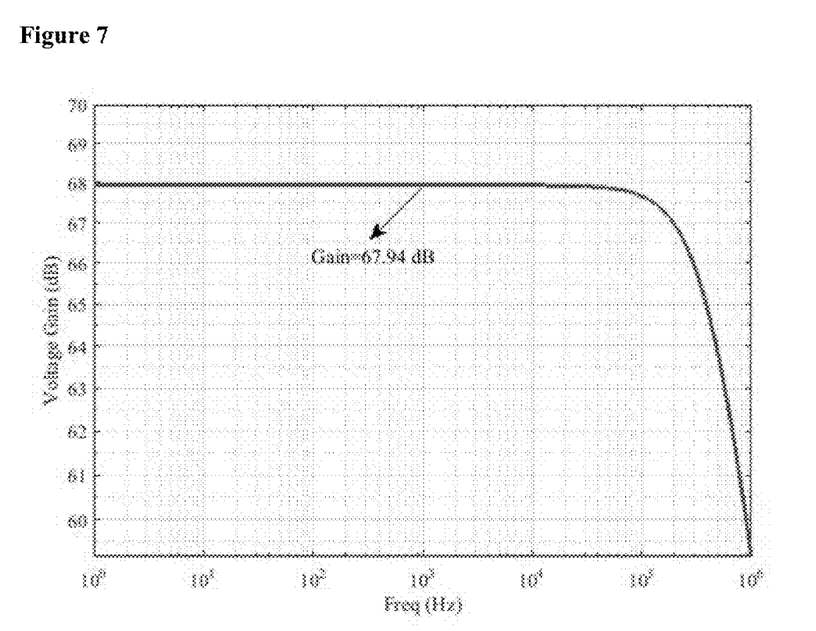
FIG. 7 shows a frequency response of the two-stage voltage comparator.

The voltage comparator structure used in the FSCU is seen in FIG. 6. Two of these telescopic voltage comparators were employed to compare the output voltages of the CS amplifiers with reference values. The comparator seen in FIG. 6 has a DC gain of 67.94 dB as seen in FIG. 7. Table III shows the main characteristics of the telescopic voltage comparator.

TABLE III

Two-stage comparator characteristics

| Parameter | Value |
|---|---|
| DC Gain | 67.94 dB |
| Unity Gain Bandwidth | 381.8 MHz |
| Power Consumption | 50.44 µW |
| Supply Voltage | 1.8 V |

The combination of the DC gains of CS amplifier and the voltage comparator results in a gain higher than 100 dB which provides desirable output waveforms at the output of the voltage comparator. Table IV contains the transistor dimensions in the comparator structure.

TABLE IV

Two-stage comparator transistor dimensions

| Transistor | Aspect Ratio (w/l) |
|---|---|
| $M_0$ | 31.4 |
| $M_{1,2}$ | 150.6 |
| $M_{3,4}$ | 150.6 |
| $M_{5,6}$ | 277.8 |
| $M_{7,8}$ | 2.45 |

Frequency Difference Detector (FDD) Unit

When the frequency sweep phase ends, and the control signal which indicates the current input frequencies are equal to the desired cutoff frequency, the frequency difference detection phase starts. The duty of the FDD unit is to compare the two output frequencies of the two CS amplifiers, and produce a signal which is proportional to the frequency difference, that is a measure of the difference between the two Miller capacitors.

Figure 9:
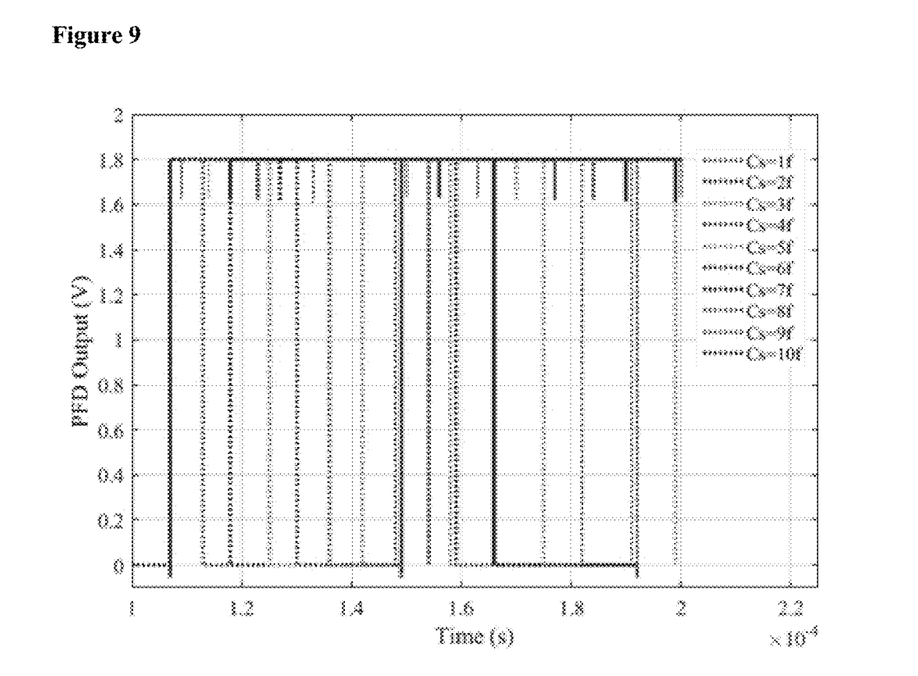
FIG. 9 shows an output pulse width of the capacitance measurement technique for $C_{sen}=0-10$ fF and $C_{ref}=10$ fF.

To compare the two output frequencies of CS amplifiers, the outputs of the amplifiers were fed into the FDD unit. The FDD unit is composed of two identical voltage comparators and a phase-frequency detector (PFD). The two comparators in the FDD unit transfer the two outputs of the voltage amplifiers to square waveforms with the same frequency. The outputs of these comparators, are applied to a PFD. The PFD output waveform has a pulse width that is proportional to the difference of the two input frequencies. Since the two inputs of the PFD are equal to the high cutoff frequencies of CS amplifiers, the pulse width of the output of PFD is proportional to the difference of high cutoff frequencies and is an indicator of the sensed capacitance. The structure of the PFD and the output waveform of the PFD for different input frequencies are seen in FIGS. 8 and 9 respectively. As seen in FIG. 9, the output pulse width of the PFD was changed due to sensing capacitance variations. A portion of the output of the PFD block is reported in FIG. 9, to illustrate the functionality of the concept.

Simulation Results

Figure 10:
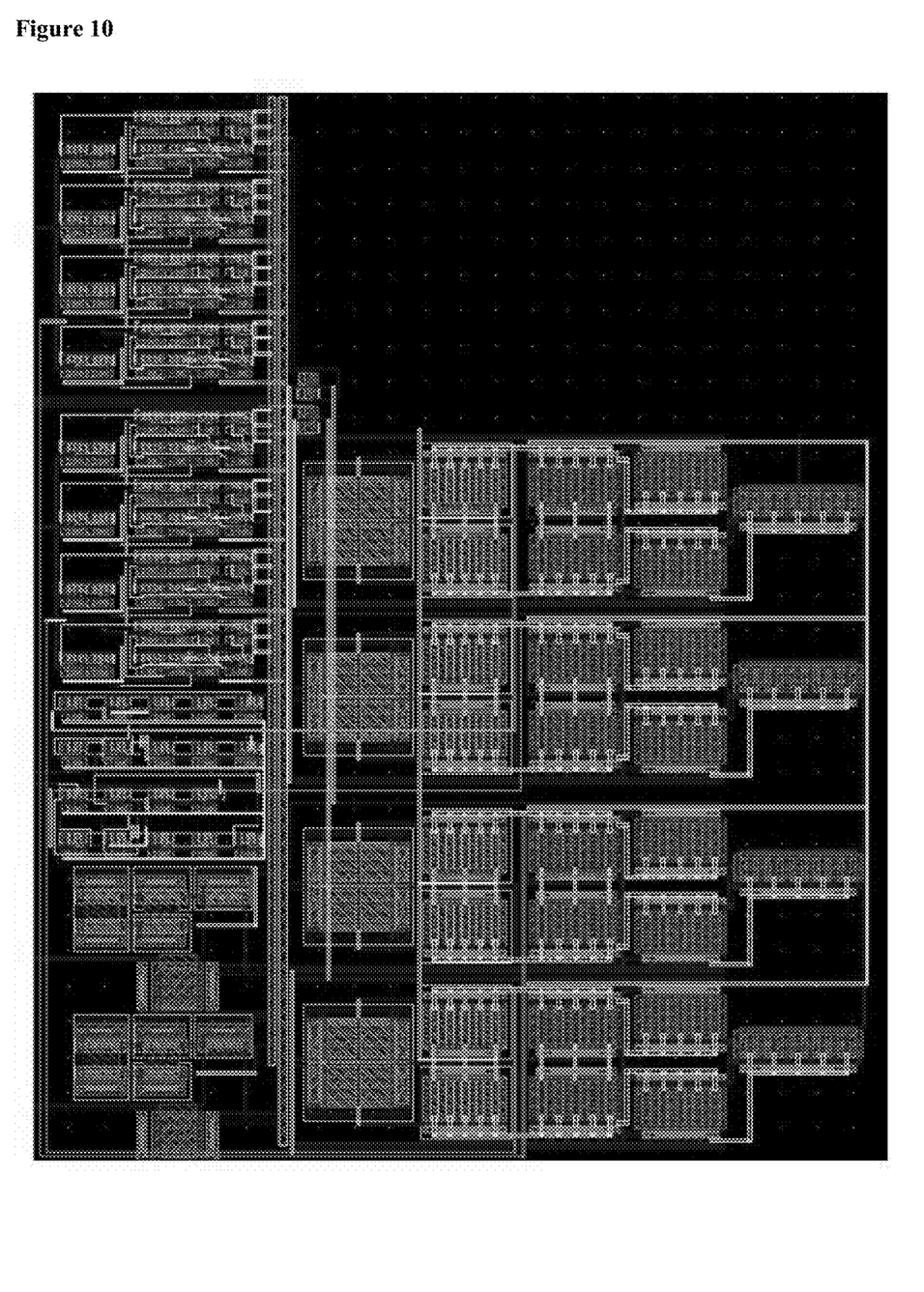
FIG. 10 shows a layout image of a structure.
Figure 11:
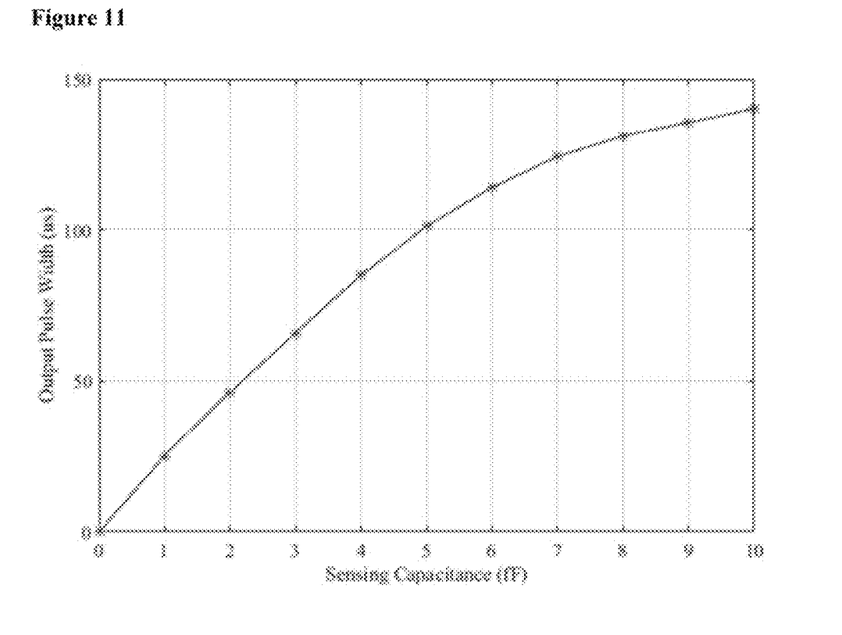
FIG. 11 shows an output pulse width of the architecture for different sensing capacitances.
Figure 12:
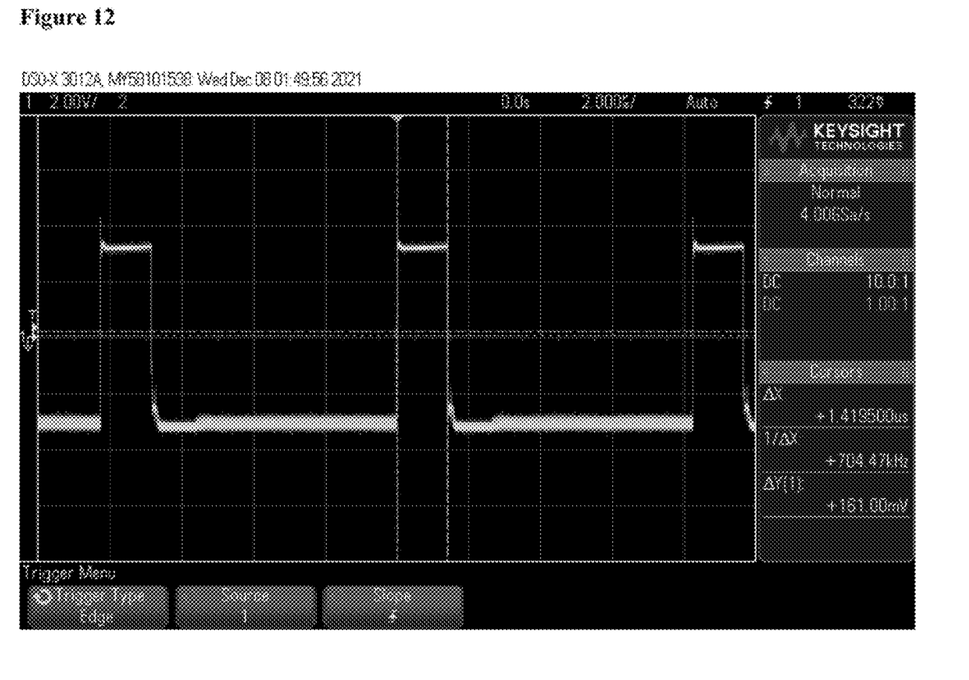
FIG. 12 shows an output pulse width for $C_s=2$ pF.
Figure 13:
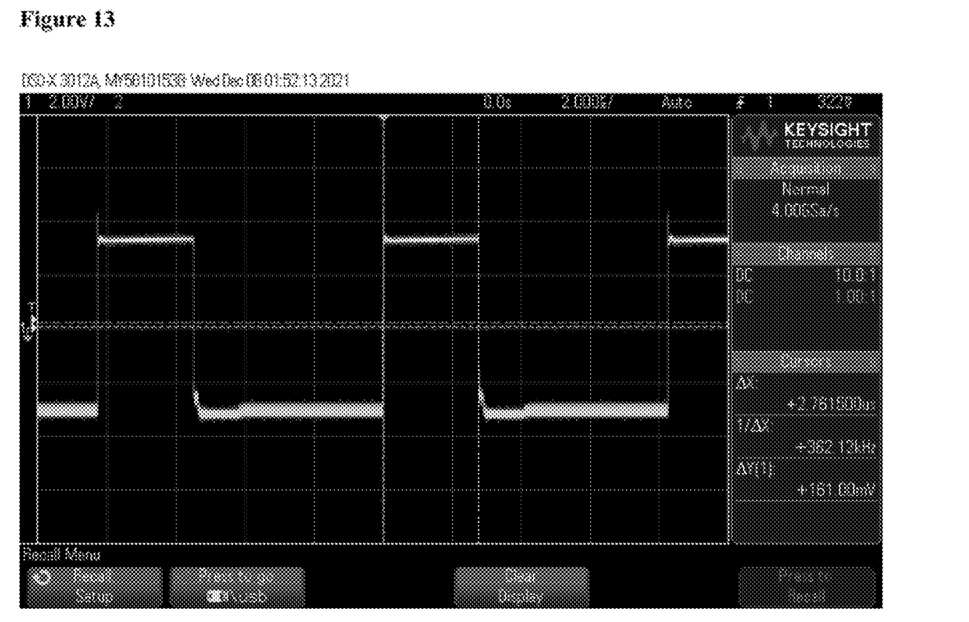
FIG. 13 shows an output pulse width for $C_s=4$ pF.
Figure 14:
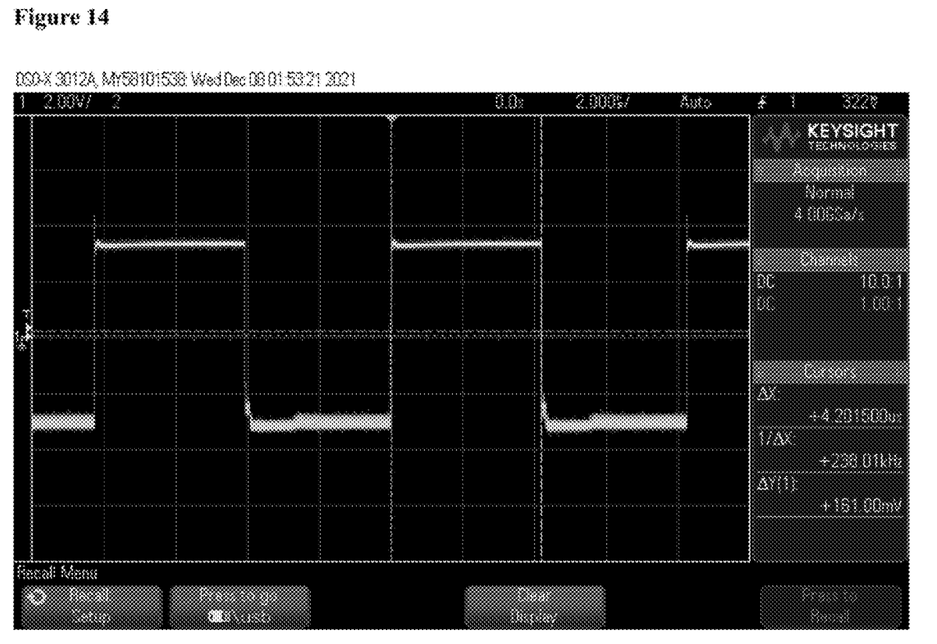
FIG. 14 shows an output pulse width for $C_s=6$ pF.
Figure 15:
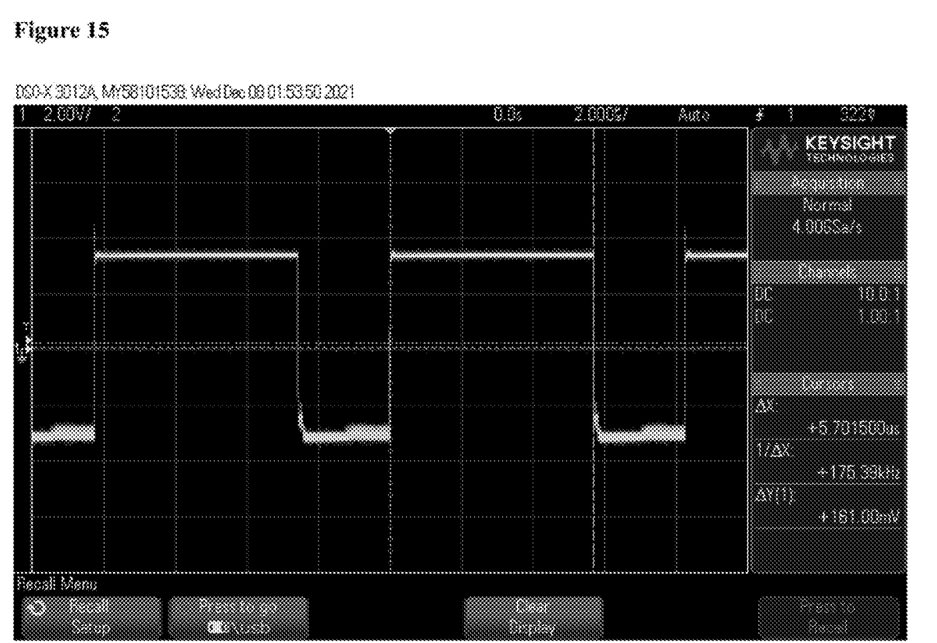
FIG. 15 shows an output pulse width for $C_s=8$ pF.

The concept was simulated in 180 nm CMOS technology and post-layout simulation results are discussed below. FIG. 10 shows the layout image. The architecture occupied an area of 18000 (µm)² on a chip. To evaluate the functionality of the sensing technique, the sensing capacitor was changed and the output pulse width of the PFD was measured. With $C_{ref}$=10 fF and $C_{sen}$=1-10 fF, the time domain response of the readout circuit is seen in FIG. 11. The architecture was capable of detection of capacitors as low as 1 fF.

As the sensing variable capacitance increases, the output pulse width of the PFD also increases. As seen in FIG. 11, for higher values of the sensing capacitance, the change in the output pulse width of the PFD, was decreased, and the output characteristic of the sensing system showed a saturation behavior. This may be due to the ratio of the sensing capacitance variation step, to the summation of the sensing and reference capacitance. In other words, as the ratio of the sensing capacitance to the summation of sensing and reference capacitance decreases, the increase in the output pulse width of the PFD diminishes. This behavior suggests that, for different sensing capacitance ranges, it may be preferable to have or select suitable reference capacitance. In other words, for more accurate sensing, it may be preferable that a system be configured to employ different reference capacitance values. This is why we did not layout the reference and sensing capacitors, and it was envisioned to use off-chip capacitors as the reference and sensing capacitance for testing fabricated chip for practical evaluation of the concept.

The architecture exhibited a sensitivity of 14.1 μsec/fF and power consumption of 792 μW from 1.8 V supply. The output pulse width of the FDD block may be delivered to a low pass filter to be transferred to a voltage variable if required. Table V compares some important characteristics of the architecture with recent measurement techniques.

TABLE V

Performance Comparison of the Proposed Architecture with Previous Approaches

| Ref. | Tech. | Technique | Resolution | Power | Sensitivity |
|---|---|---|---|---|---|
| [1] | 0.5 μm | CVC | 5 fF | NA | NA |
| [2] | 0.18 μm | CVC | NA | NA | 255 mV/fF |
| [7] | 0.25 μm | CFC | 10 fF | 29 mW | 11 KHz/fF |
| [9] | 0.35 μm | CFC | 2.5 fF | NA | 223 KHz/fF |
| This Work | 0.18 μm | CPC | 1 fF | 792 μW | 14.1 μsec/fF |

Table V shows that the concept employing a mechanism for capacitance variation sensing rather than traditional CFC and CVC approaches permitted for detection of smaller capacitance variation values. Moreover, previous techniques often rely on complicated system-on-chips to detect capacitance variations, where the current concept consumes less power. Sensitivity of this technique that transforms capacitance variations to pulse width could not be compared to previous techniques that do not involve such transformation.

Conclusion

Described herein is a technique based on high cutoff frequency variation of a common source amplifier for detection of small capacitance variations, and the function or operation of the technique was evaluated using simulations in 180 nm CMOS technology. It is preferable for a biosensor in life science applications that the biosensor permits operation as a sensing system capable of smaller variation detection while maintaining lower power performance. It has been appreciated that the current technique may permit detection of lower capacitance variations as low as 1 fF with a sensitivity of 14.1 μsec/fF, and a power consumption of 792 μW.

In a separate study, a circuit was implemented to test function. The readout circuit was implemented using off-the-shelf components, and the minimum available capacitors in the market that could be used were in the 1 pF range; therefore, the resolution of the implemented circuit was 1 pF. However, the resolution of the current concept is three order of magnitude higher (1 fF).

Figure 16:
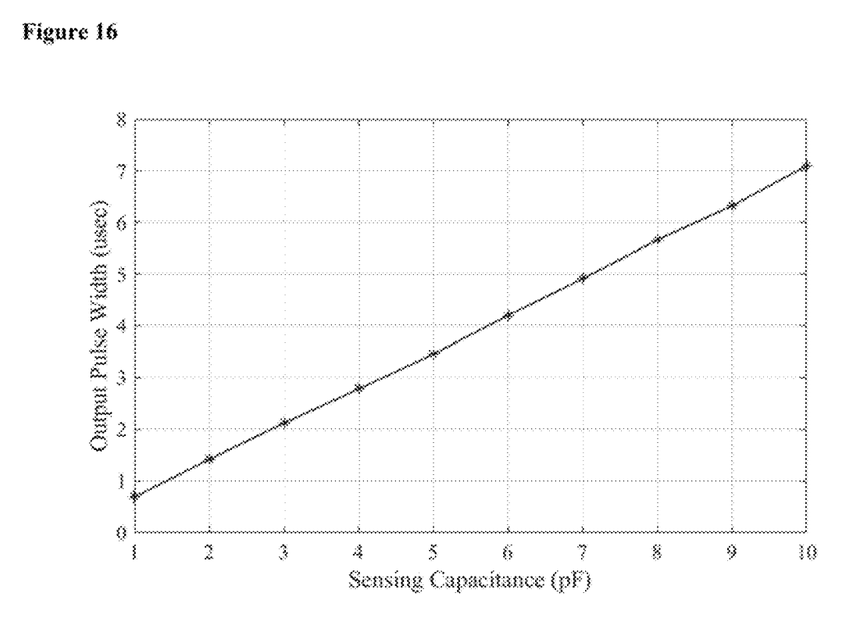
FIG. 16 shows an output characteristic for 1 pF resolution.

Considering the range and the tolerance of the available varactors in the market, the sensing capacitance was changed manually. For some of the sensing capacitors, the output pulse width is shown in FIGS. 12 to 15. Therefore, for the 1 pF resolution, the output characteristic is resulted as in FIG. 16.

While the invention has been described with reference to preferred embodiments, the invention is not or intended by the applicant to be so limited. A person skilled in the art would readily recognize and incorporate various modifications, additional elements and/or different combinations of the described components consistent with the scope of the invention as described herein.

We claim:

1. A method for measuring a capacitance change or difference of a sensing capacitor, the method comprising:
    sweeping a frequency range of first and second alternating current (AC) voltage sources respectively connected to first and second amplifiers, said first amplifier having or connected to a first reference capacitor or electrode and said second amplifier having or connected to a second reference capacitor or electrode and the sensing capacitor;
    detecting first and second high cutoff frequencies respectively of the first and second amplifiers; and
    determining a difference between the first and second high cutoff frequencies, wherein the difference reflects the capacitance change or difference.

2. The method of claim 1, wherein the first and second voltage sources are identical or substantially identical to each other, and the first and second reference capacitors or electrodes are identical or substantially identical to each other.

3. The method of claim 1, wherein the first and second amplifiers comprise first and second common source voltage amplifiers each comprising a cascode current source.

4. The method of claim 1, wherein the first and second reference capacitors are parallel or in a Miller capacitance location respectively in relation to the first and second amplifiers.

5. The method of claim 1, wherein the sensing capacitor is parallel to the second reference capacitor.

6. The method of claim 1, wherein said detecting the first and second high cutoff frequencies comprises comparing first and second output voltages respectively from the first and second amplifiers to respective first and second reference voltage values, and stopping said sweeping the frequency range when said comparing the first and second output voltages indicates the first and second high cutoff frequencies are reached, wherein the first and second reference voltage values comprise or are based on first and second maximum output voltages respectively of the first and second amplifiers.

7. The method of claim 1, further comprising producing a third output voltage having a period proportional to the difference.

8. The method of claim 7, wherein said determining the difference comprises transforming the first and second high cutoff frequencies to first and second square waveforms, and said producing the third output voltage comprises producing the third output voltage with an output voltage waveform having a pulse width proportional to the difference.

9. The method of claim 7, further comprising providing the third output voltage to a low pass filter.

10. The method of claim 1, wherein the sensing capacitor comprises a CMOS biosensor.

11. A system for measuring a capacitance change or difference of a sensing capacitor, the system comprising:
    first and second alternating current (AC) voltage sources;
    first and second voltage amplifiers respectively connected to the first and second voltage sources, said first amplifier having or connected to a first reference capacitor or electrode and said second amplifier having or connected to a second reference capacitor or electrode and the sensing capacitor;
    a frequency sweep control unit for sweeping a frequency range of the first and second voltage sources and detecting first and second high cutoff frequencies respectively of the first and second amplifiers; and a frequency difference detector for determining a difference between the first and second high cutoff frequencies, wherein the difference reflects the capacitance change or difference.

12. The system of claim 11, wherein the first and second voltage sources are identical or substantially identical to each other, and the first and second reference capacitors or electrodes are identical or substantially identical to each other.

13. The system of claim 11, wherein the first and second voltage amplifiers comprise first and second common source voltage amplifiers each comprising a cascode current source.

14. The method of claim 11, wherein the first and second reference capacitors are parallel or in a Miller capacitance location respectively in relation to the first and second voltage amplifiers.

15. The system of claim 11, wherein the sensing capacitor is parallel to the second reference capacitor.

16. The system of claim 11, wherein the first and second voltage sources and the first and second voltage amplifiers are arranged as seen in a block diagram illustrated in FIG. 1 or 2.

17. The system of claim 11, wherein the frequency sweep control unit comprises first and second voltage comparators and first and second frequency lock detectors respectively connected to the first and second voltage comparators, wherein said first and second voltage comparators are respectively for comparing first and second output voltages respectively from the first and second voltage amplifiers to respective first and second reference voltage values, and said first and second frequency lock detectors are for stopping said sweeping the frequency range and signalling the frequency difference detector to determine the difference upon determining that the first and second high cutoff frequencies are reached, wherein the first and second reference voltage values comprise first and second maximum output voltages respectively of the first and second voltage amplifiers.

18. The system of claim 17, wherein each said first and second voltage comparators comprise components or a circuit as illustrated in FIG. 6.

19. The system of claim 17, wherein the first and second frequency lock detectors comprise respective first and second counters and respective first and second frequency lock detection flags, wherein each said first counter and frequency lock detection flag and second counter and frequency lock detection flag are arranged as illustrated in FIG. 5.

20. The system of claim 11, wherein the frequency difference detector comprises third and fourth voltage comparators and a phase frequency detector connected to the third and fourth voltage comparators, wherein the third and fourth voltage comparators are for transforming the first and second high cutoff frequencies to first and second square waveforms, and the phase frequency detector is for producing a third output voltage with an output voltage waveform having a pulse width proportional to the difference.

21. The system of claim 20, further comprising a low pass filter arranged to receive the third output voltage from the phase frequency detector.

22. The system of claim 11, wherein the first and second reference capacitors and the sensing capacitor comprise off-chip first and second reference capacitors and the sensing capacitor.

23. The system of claim 11, wherein the sensing capacitor comprises a CMOS biosensor.

24. A method for measuring a capacitance change or difference of a sensing capacitor, the method comprising detecting a high cutoff frequency of an amplifier connected to a voltage source, a reference capacitor and the sensing capacitor, and determining a difference between the high cutoff frequency and a reference high cutoff frequency, wherein the difference reflects the capacitance change or difference, and wherein the reference high cutoff frequency is detected from a further amplifier connected to a further voltage source and a further reference capacitor, the further amplifier, the further voltage source and the further reference capacitor being identical or substantially identical respectively to the amplifier, the voltage source and the reference capacitor.

* * * * *